United States Patent
Raynal et al.

(10) Patent No.: US 10,143,372 B1
(45) Date of Patent: Dec. 4, 2018

(54) EXIT PUPIL LOCATOR TOOL

(71) Applicant: Rockwell Collins, Inc., Cedar Rapids, IA (US)

(72) Inventors: Francois Raynal, Portland, OR (US); Bobby D. Foote, Marion, IA (US)

(73) Assignee: ROCKWELL COLLINS, INC., Cedar Rapids, IA (US)

( * ) Notice: Subject to any disclaimer, the term of this patent is extended or adjusted under 35 U.S.C. 154(b) by 160 days.

(21) Appl. No.: 15/365,900

(22) Filed: Nov. 30, 2016

(51) Int. Cl.
| | |
|---|---|
| *A61B 3/15* | (2006.01) |
| *G02B 27/01* | (2006.01) |
| *G02B 27/32* | (2006.01) |
| *G01B 11/27* | (2006.01) |
| *A42B 3/04* | (2006.01) |
| *G02C 5/00* | (2006.01) |

(52) U.S. Cl.
CPC .............. *A61B 3/152* (2013.01); *A42B 3/042* (2013.01); *G01B 11/27* (2013.01); *G02B 27/0172* (2013.01); *G02B 27/0176* (2013.01); *G02B 27/32* (2013.01); *G02C 5/001* (2013.01); *G02B 2027/0161* (2013.01)

(58) Field of Classification Search
CPC ......... A61B 3/152; A42B 3/042; G01B 11/27; G02B 27/0172; G02B 27/0176; G02B 27/32; G02B 2027/0161; G02C 5/001

USPC .................. 351/41, 158, 159.75–159.77, 211
See application file for complete search history.

(56) References Cited

U.S. PATENT DOCUMENTS

| 9,244,280 B1 * | 1/2016 | Tiana ................. G02B 27/0172 |
| 2002/0020004 A1 * | 2/2002 | Beautz ................... A42C 2/007 2/422 |
| 2004/0163228 A1 * | 8/2004 | Piorkowski ............ A42C 2/007 29/407.04 |

OTHER PUBLICATIONS

Foote "Design guidelines for advanced air-to-air helmet-mounted display systems" Proc. SPIE 3362, Helmet- and Head-Mounted Displays III; Aug. 11, 1998.*

* cited by examiner

*Primary Examiner* — Zachary Wilkes
*Assistant Examiner* — George G King
(74) *Attorney, Agent, or Firm* — Donna P. Suchy; Daniel M. Barbieri

(57) ABSTRACT

An exit pupil locator tool including a connector and a target. The connector is configured to engage an optics component that defines an optics axis of a helmet mounted display. The target includes a reticle, a first aperture, and a second aperture and defines a tool axis that is arranged at an oblique tool angle relative to the optics axis.

20 Claims, 9 Drawing Sheets

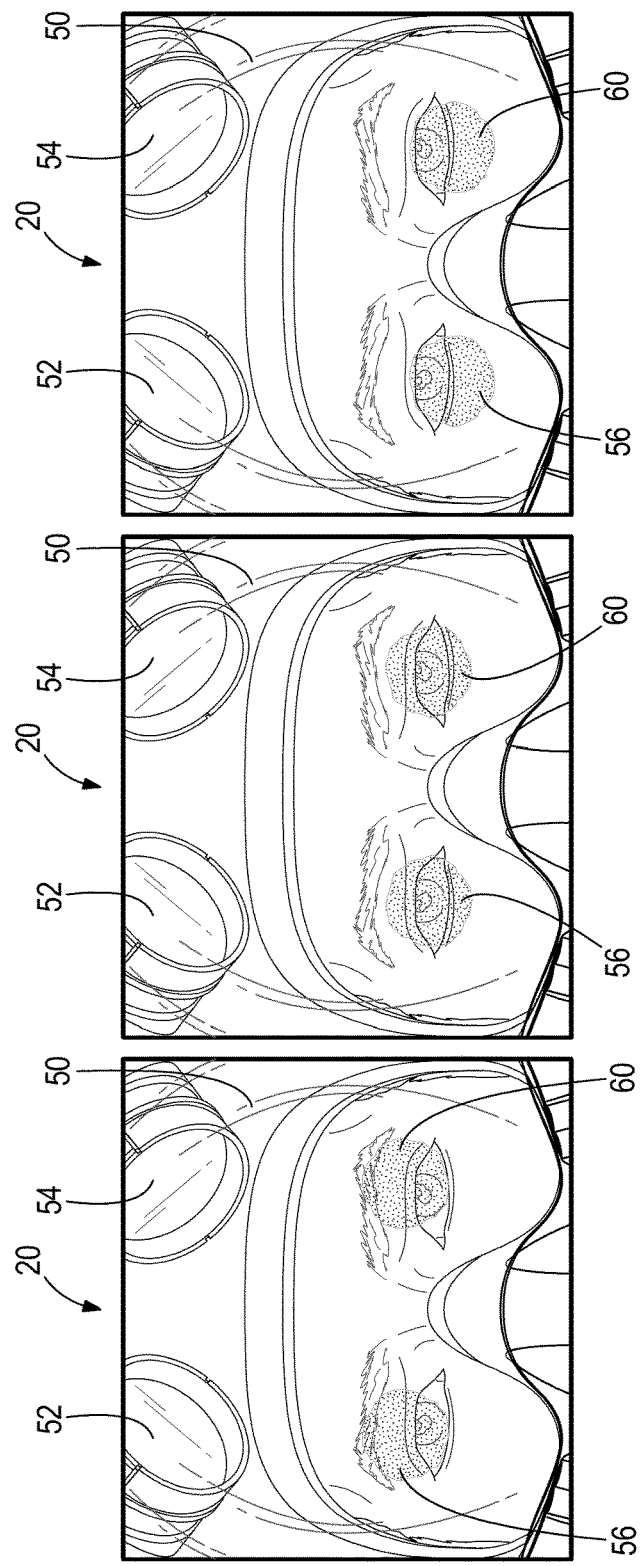

EXIT PUPIL LOCATOR TOOL

BACKGROUND

The present disclosure relates generally to the field of helmet mounted displays (HMD). A HMD may be used by an operator in an aircraft to allow the operator to have a view of the outside world with superimposed information, such as symbols and images captured by sensors.

Helmet mounted displays (HMDs), are used in aircraft applications, both in in-flight applications and in flight simulators. Proper alignment and fitting of HMDs is important for achieving successful use of the HMD.

SUMMARY

In one aspect, embodiments of the inventive concepts disclosed herein are directed to an exit pupil locator tool. The exit pupil locator tool includes a connector and a target. The connector is configured to engage an optics component that defines an optics axis of a helmet mounted display. The target includes a reticle, a first aperture, and a second aperture and defines a tool axis that is arranged at an oblique tool angle relative to the optics axis In a further aspect, embodiments of the inventive concepts disclosed herein are directed to a fitting system for a helmet comprising a helmet mounted display having a computer, an image source, an optics component, and a combiner. The fitting system includes an exit pupil locator tool that includes a connecting feature configured to engage the optical component, a reticle configured to receive light from the optical component, a first aperture positioned downstream of the reticle to receive light from the reticle, and a second aperture positioned downstream of the first aperture and configured to project a targeting image onto the combiner.

In a further aspect, embodiments of the inventive concepts disclosed herein are directed to a method of fitting a helmet that includes a helmet mounted display. The method includes installing an exit pupil locator tool onto an optics component of the helmet mounted display, projecting light into the exit pupil locator tool, projecting a reticle shaped targeting image onto a combiner of the helmet mounted display with the exit pupil locator tool, observing a reflection of the targeting image on a user's eye, and determining a differential distance between a center of the targeting image and the user's eye.

BRIEF DESCRIPTION OF THE DRAWINGS

Exemplary embodiments will become more fully understood from the following detailed description, taken in conjunction with the accompanying drawings, wherein like reference numerals refer to like elements, and:

FIG. 3 is a front view of the HMD of FIG. 2 in a first configuration according to one embodiment;

FIG. 4 is a front view of the HMD of FIG. 2 in a second configuration according to one embodiment;

FIG. 5 is a front view of the HMD of FIG. 2 in a third configuration according to one embodiment;

DETAILED DESCRIPTION

Referring generally to the FIGURES, systems for and methods of fitting and aligning a worn display are described according to some exemplary embodiments. Worn displays and in particular Helmet Mounted Displays (HMDs) produce an exit pupil. The methods and systems advantageously match the end user's eye position relative to a HMD without removing the display from service and provides higher accuracy than is possible using conventional factory calibration in some embodiments. In some embodiments, the systems for and methods of include the use of an exit pupil locator tool that attaches to an optics component of the HMD during fitting and is easily removable after fitting is complete. The exit pupil locator tool improves accuracy and consistency in positioning the exit pupil on the user's eye.

Figure 1:
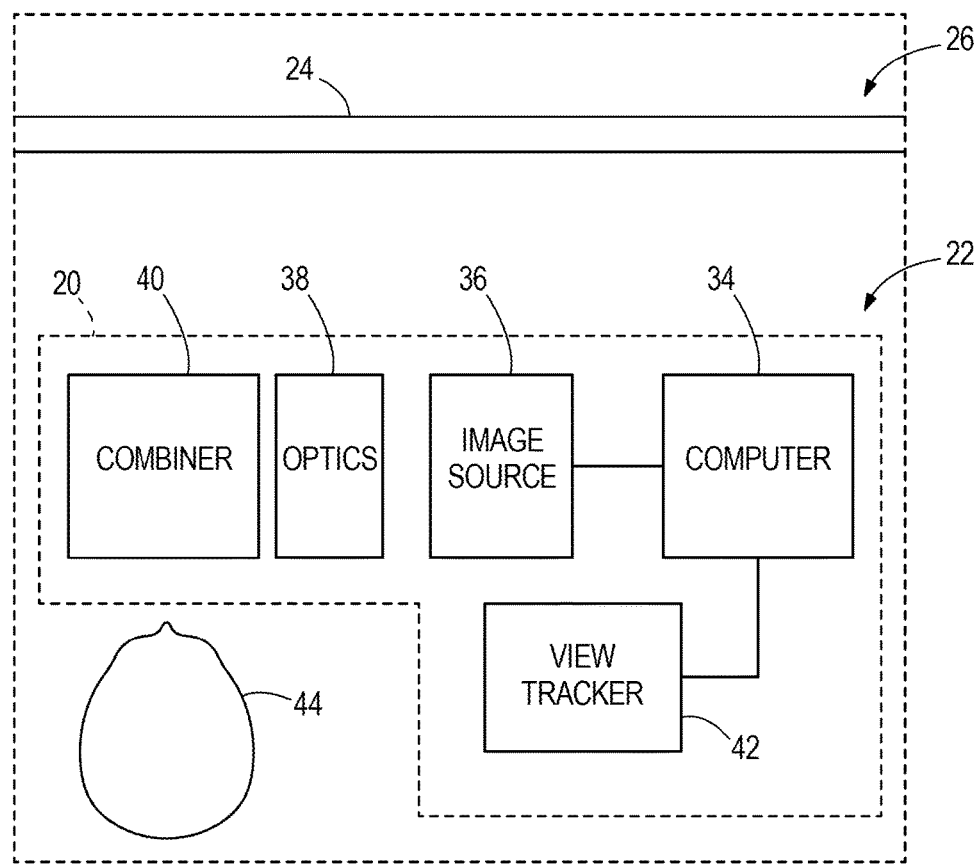
FIG. 1 is a schematic view of a virtual display system including a near eye combiner according to one embodiment.

As shown in FIG. 1, a HMD system 20 provides an image at one or more locations in an internal environment 22. The HMD system 20 is part of a helmet or other headgear in some embodiments, but may be a part of another worn equipment of clothing. The HMD system 20 can be utilized in various applications, including but not limited to aviation, medical, naval, targeting, ground-based vehicle, military, remote control, etc. In one embodiment, the HMD system 20 is configured for use in smaller cockpit embodiments, for use in remote vehicle or aircraft applications, for use in ships or boats, or for use in simulators or other training devices. The HMD system 20 can be utilized for two dimensional or three dimensional images.

The HMD system 20 is disposed in the internal environment 22 which can be a cockpit, bridge, operating room, etc. The illustrated internal environment 22 includes a window or port (e.g., a windshield or canopy 24) to an external environment 26 external to the internal environment 22. For example, the internal environment 22 can be an aircraft cockpit, and the external environment 26 can be the real world viewable through the canopy 24 of the cockpit. In one embodiment, the internal environment 22 is a windowless cockpit environment and the windshield canopy is eliminated. In one embodiment, the HMD system 20 is a joint task force fighter helmet HMD.

In some embodiments, the HMD system 20 includes a computer 34, an image source 36, optics 38, and a combiner 40. Images from the image source 36 are projected via the optics 38 to the combiner 40 which can be in the form of a helmet visor. The HMD system 20 also includes a view tracker 42 for providing gaze information associated with a user 44 (e.g., pilot) to the computer 34. In some embodiments, the view tracker 42 is not included with the HMD system 20.

In operation, the HMD system 20 provides images from the image source 36 to the user 44 so that they can simultaneously view the images provided by the HMD system 20 and a real world scene through the canopy 24. The images can include graphic and/or text information (e.g., flight path vector, target icons, symbols, fuel indicators, course deviation indicator, pitch indicator, etc.). The image can also include information from other sensors or equipment associated with the internal environment 22 and/or the external environment 26 (e.g., a vertical traffic collision avoidance display, terrain avoidance and awareness display, a weather radar display, flight control sensors, an electronic flight bag, a navigation system, environmental sensors, etc. in an aircraft). In addition, the images can include synthetic or enhanced vision images. In one embodiment, collimated light representing the image from the image source 36 is provided on combiner 40 so that the pilot can view the image conformally on the real world scene through combiner 40.

Figure 2:
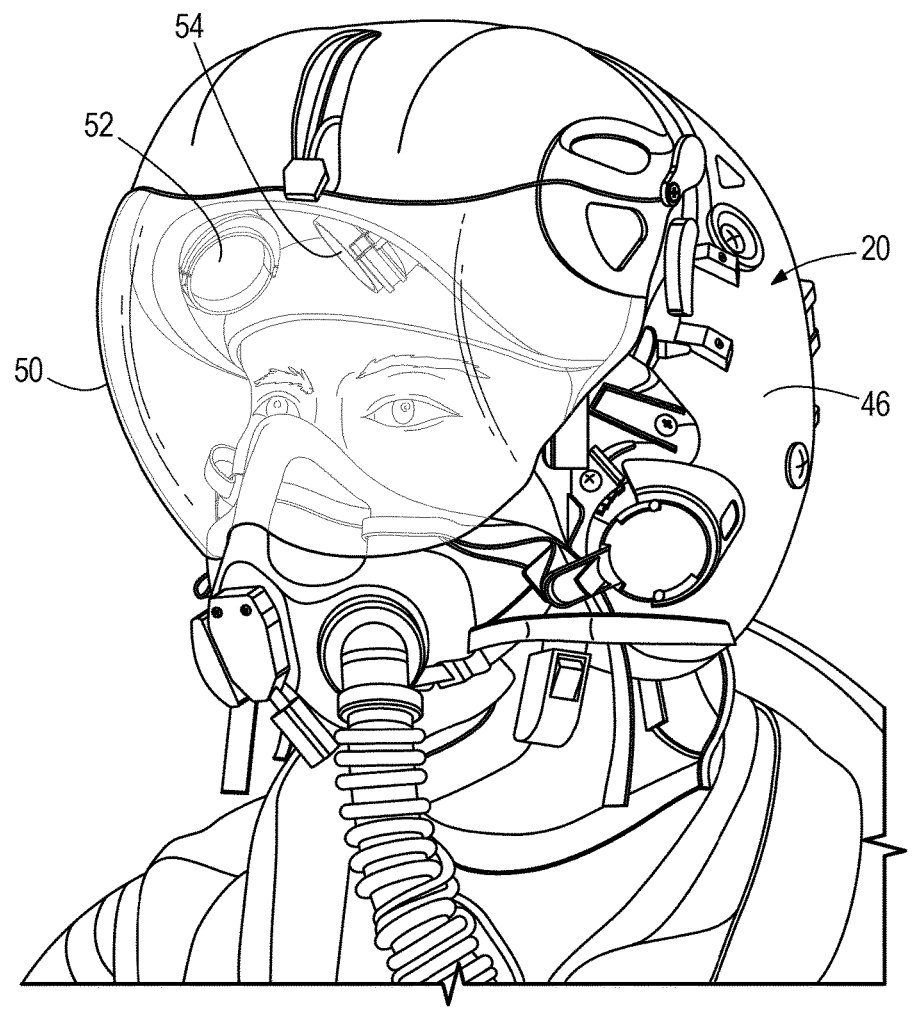
FIG. 2 is a perspective view of a helmet including a helmet mounted display (HMD) according to one embodiment.

As shown in FIG. 2, a helmet 46 includes the HMD system 20 and houses the computer 34 (see FIG. 1), the image source 36, the optics 38, and the combiner 40 in the form of a visor 50. The optics 38 include a first optics component 52 and a second optics component 54. In one embodiment, the first optics component 52 projects an image onto the visor 50 and is directed to the user's right eye. In one embodiment, the second optics component 54 projects an image onto the visor 50 and is directed to the user's left eye. In other embodiments, the HMD system 20 may include only one optics component arranged to project images for the consumption of both the user's eyes.

As shown in FIG. 3, the HMD system 20 produces images that are collimated light sources and present a first exit pupil 56 associated with the first optics component 52 and a second exit pupil 60 associated with the second optics component 54. The produced images appear to the user 44 as objects within the external environment 26 (i.e., spaced away from the visor 50). In order to produce images on the visor 50 that are clearly visible to the user 44, the first exit pupil 56 is preferably aligned with the user's right eye and the second exit pupil 60 is preferably aligned with the user's left eye. In one preferred embodiment, the center of the first exit pupil 56 is within two millimeters (2 mm) of the center of the user's right eye, and the center of the second exit pupil 60 is within two millimeters (2 mm) of the center of the user's left eye. In other embodiments, the center of the first exit pupil 56 is within four millimeters (4 mm) of the center of the user's right eye, and the center of the second exit pupil 60 is within four millimeters (4 mm) of the center of the user's left eye. In still other embodiments, the center of the first exit pupil 56 is within eight millimeters (8 mm) of the center of the user's right eye, and the center of the second exit pupil 60 is within eight millimeters (8 mm) of the center of the user's left eye. The alignment shown in FIG. 3 is acceptable and the center of the first exit pupil 56 is within four millimeters of the center of the user's right eye, and the center of the second exit pupil 60 is within four millimeters of the center of the user's left eye.

In order to align the exit pupils 56, 60 to the user's eyes, the HMD system 20 is custom fit to each user's head. The process involves scanning the user's head to create a 3D model of the user's head. A fit liner is then custom milled to fit within the helmet 46 and the visor 50 is custom milled in order to align the user's eyes with the exit pupils 56, 60 and to provide a comfortable fit for the user 44. After an initial fitting, an individual fitter or a fitter team will view the alignment of the first exit pupil 56 and the user's right eye and the alignment of the second exit pupil 60 with the user's left eye. Based on the fitter's evaluation, the fit liner is then adjusted to bring the exit pupils 56, 6 into alignment. In some embodiments, the fit of the helmet 46 is adjusted using pads, rigid inserts, gel inserts, air bladders, high density foam, or other impact absorbing materials that are suitable for helmet construction. The placement of inserts or pads can be used to raise, lower, tilt, rotate, or move the helmet 46 side-to-side relative to the user's head and thereby adjust the position of the user's eyes relative to the exit pupils 56, 60.

As shown in FIG. 4, human error in the fitting process can lead to misalignment of the exit pupils 56, 60 and the user's eyes. The example shown in FIG. 4 shows the exit pupils 56, 60 arranged above the user's eyes, and the example shown in FIG. 5 shows the exit pupils 56, 60 arranged below the user's eyes. In addition, to vertical misalignment, horizontal misalignment can also occur. The alignment in this method of fitting is dependent of the fitters judgement and is made difficult by the large and non-uniform shape of the exit pupils 56, 60. The size of the exit pupils 56, 60 is relatively large and often oblong in shape. For example, the exit pupils 56, 60 typically define an approximate diameter of about twenty-five millimeters.

Finding the center of the exit pupils 56, 60 can be difficult for the fitter and is a subjective determination that can lead to alignment outside of acceptable tolerances (e.g., within four millimeters of center) and resulting in lower display performance and potential loss of display in high G maneuvers (e.g., in a fighter jet). In one embodiment, when a fighter pilot is the user 44, and is experiencing a high G situation, the helmet 46 will tend to shift slightly on the pilot's head. These small positional shifts of the helmet 46 do not significantly affect performance of the HMD system 20 when the exit pupils 56, 60 are aligned with the center of the pilots eyes within a predetermined tolerance (e.g., four millimeters). However, if the pilot initiates a strong dive maneuver and the helmet 46 is shifted slightly upward on the pilot's head during the high G situation caused by the dive, the alignment shown in FIG. 4 may cause a loss of visibility of the digital images during the dive maneuver. This challenge is further exacerbated by multiple number of fitting facilities that exist, and a large number of fitters (e.g., over one hundred different fitters) all having various levels of skills in fitting.

Figure 6:
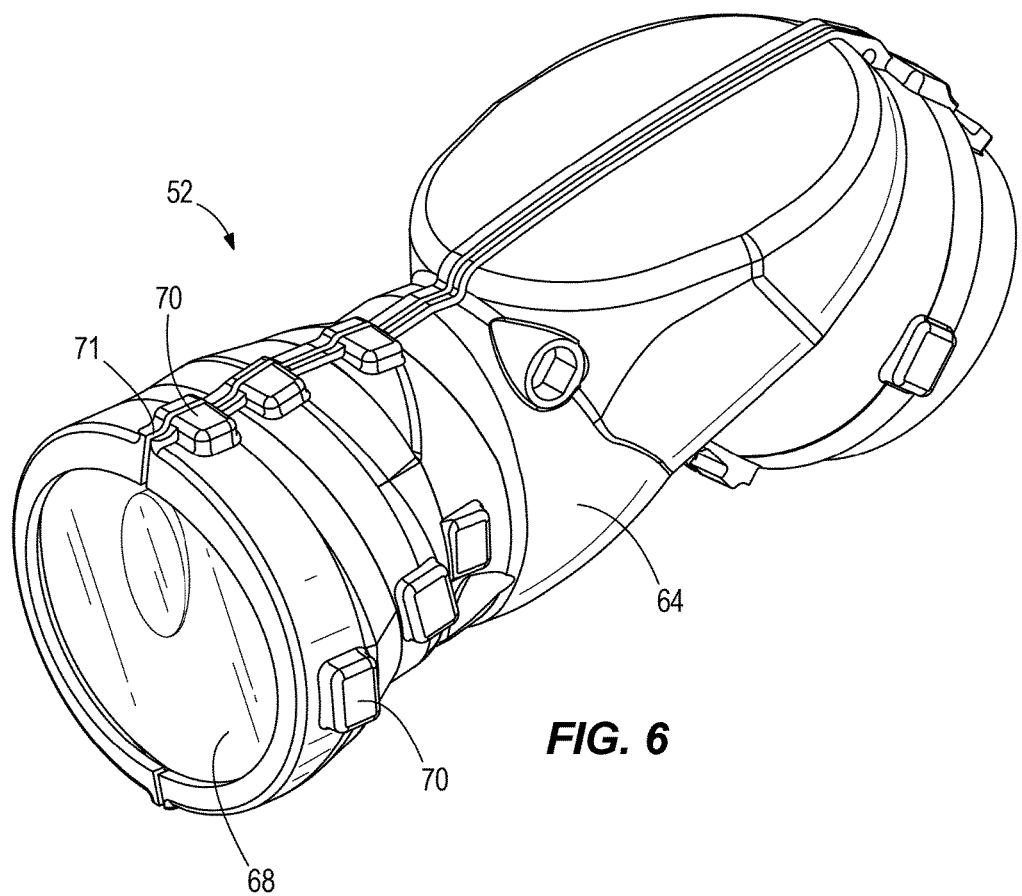
FIG. 6 is a pictorial view of the optic component of FIG. 6 with the exit pupil locator removed according to one embodiment.

As shown in FIG. 6, the first optics component 52 includes an optics body 64 and an output lens 68. The optics body includes a locating feature in the form of four primary projections 70 and two offset projections 71 (only one is visible in FIG. 6). Below, only the first optics component 52 and related methods and components will be described. The second optics component 54 is substantially identical to the first optics component 52 and includes similar parts. The first optics component 52 is arranged to produce an off-axis light pattern exiting the output lens 68. In some embodiments, the images projected out of the output lens 68 strikes the visor 50 at an oblique angle rather than substantially perpendicularly to the visor 50. The incident light (e.g., image) is not parallel to the axis of the optical system (i.e., the user's line of sight). The first optics component 52 is only one example of an optics component and is not meant to be a limiting example. The optics component may take on many forms and structures within the context of this disclosure. For example, the locating feature may include more projections, may include one or more recesses, may be a spline or keyway, may include threads or may be eliminated. The optics body 64 may have a different shape or be arranged differently, as desired.

Figure 7:
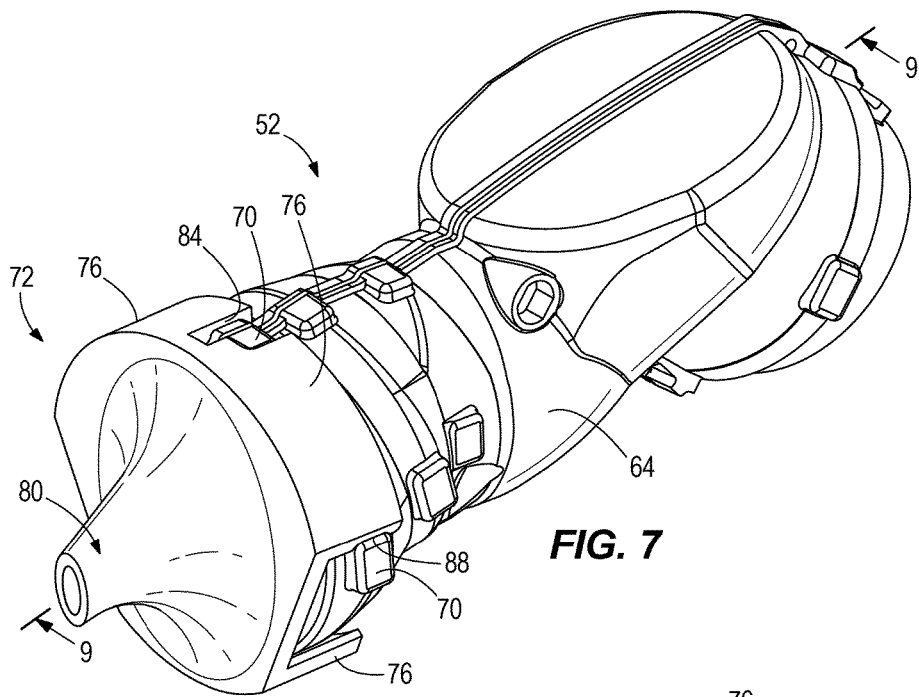
FIG. 7 is a pictorial view of an optic component of the HMD of FIG. 2 and an exit pupil locator according to one embodiment.

As shown in FIG. 7, an exit pupil locator tool 72 is coupled to the optics body 64 and includes a connector or connecting feature in the form of two tabs 76 arranged to engage the optics body 64, and a target or targeting feature 80. The tabs 76 are sized to engage the optics body 64 with a light interference fit such that the exit pupil locator tool 72 is easily installed onto, and removed from, the optics body 64 while providing a secure connection when installed. In other embodiments, the connecting feature may include more than two or may include a single annular wall, or may include another fastening architecture such as threads, snap fit, or another coupling.

As also shown in FIG. 7, a locating feature in the form of two diametrically opposed slots or recesses 84, one recess 84 arranged in each tabs 76, is sized to receive the primary projection 70 and the offset projection 71. The locating feature also includes two diametrically opposed recesses 88, each arranged to engage a primary projection 70. The offset projections 71 are arranged such that the exit pupil locator tool 72 can only be engaged with the optics body 64 in the desired orientation.

Figure 8:
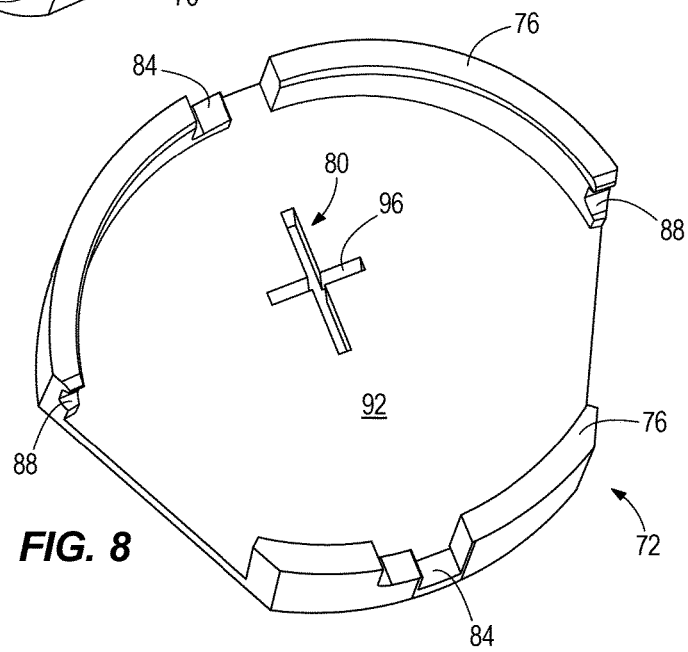
FIG. 8 is a back view of the exit pupil locator of FIG. 7 according to one embodiment.

As shown in FIG. 8, the exit pupil locator tool 72 includes a substantially planar mating face 92 that is arranged to engage the optics body 64 when the exit pupil locator tool 72 is installed on the optics body 64. The targeting feature 80 includes a reticle 96 arranged to receive the image from the first optics component 52. In the illustrated embodiment, the reticle 96 defines a cross, X, or tee-shape. In other embodiments, the reticle 96 can define a different shape, such as a square, a star, a dot, concentric circles, or other shapes.

Figure 9:
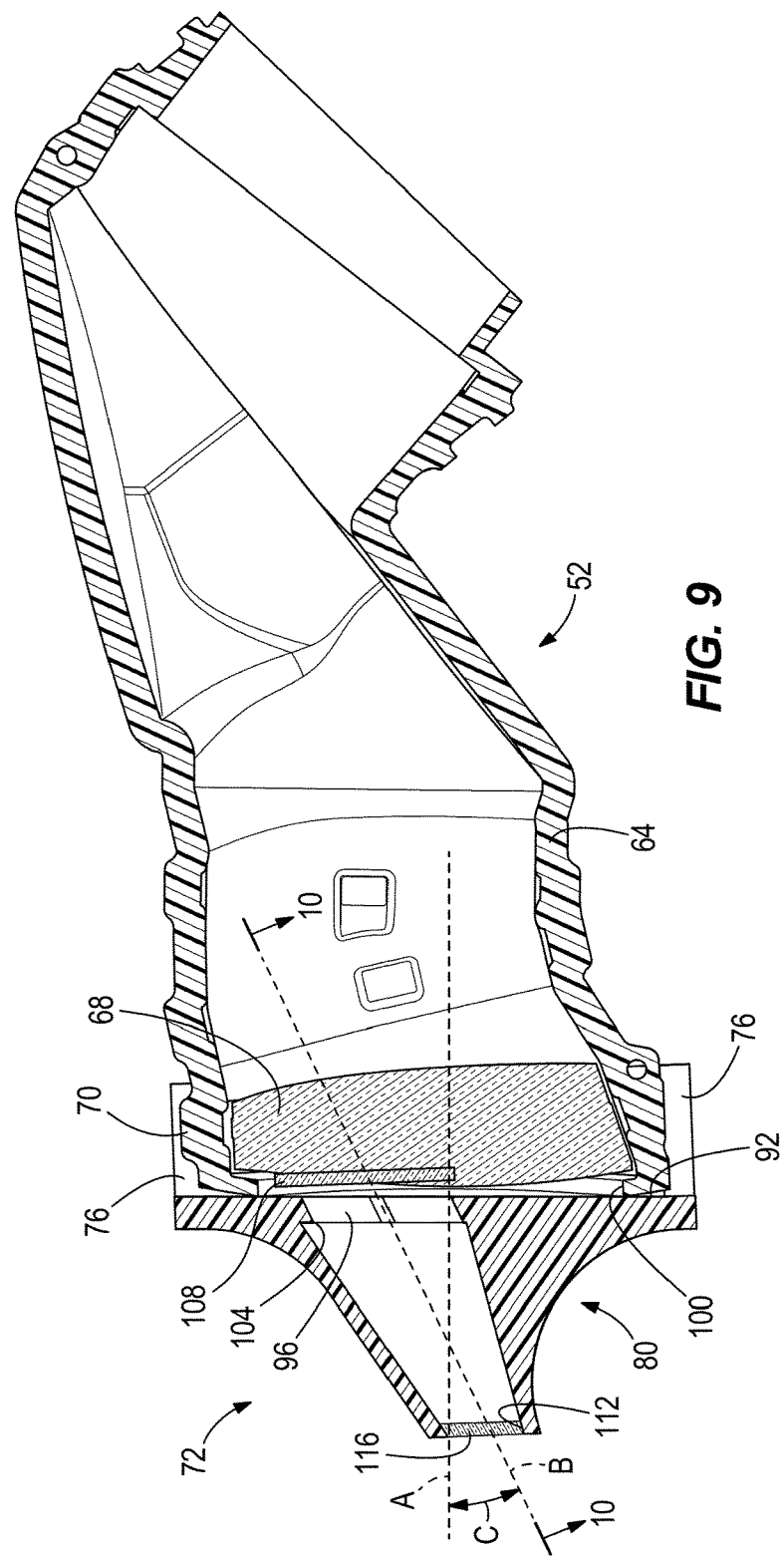
FIG. 9 is a cross sectional view of the optic component and exit pupil locator of FIG. 7 taken along line 9-9 in FIG. 7.
Figure 10:
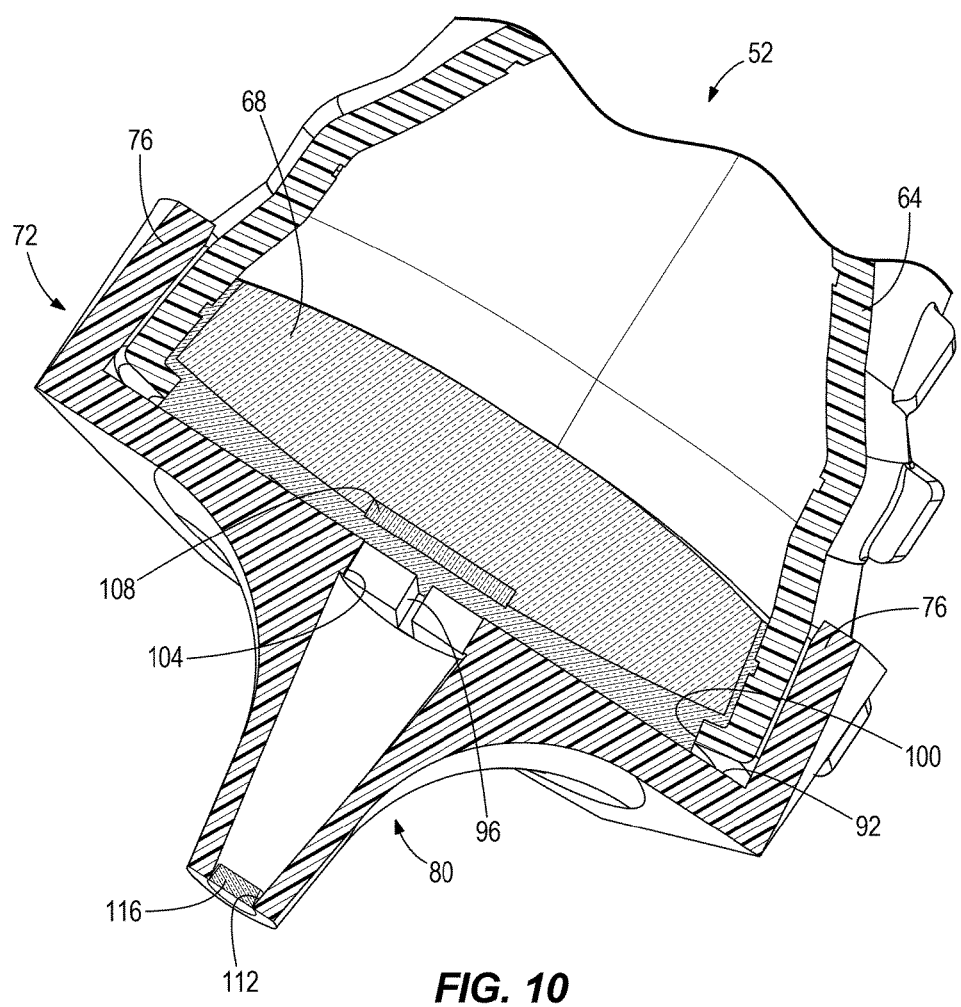
FIG. 10 is a section view of the optic component and exit pupil locator of FIG. 7 taken along line 10-10 in FIG. 9.

As shown in FIG. 9, the optics component 52 defines a perpendicular optics axis A that is perpendicular to an outlet 100 of the optics body 64 adjacent the output lens 68 and centered in the outlet 100. When the exit pupil locator tool 72 is installed, the perpendicular optics axis A is also perpendicular to the mating face 92. The targeting feature 80 includes the reticle 96, a first aperture 104, a first lens 108 associated with the first aperture 104, a second aperture 112, and a second lens 116 associated with the second aperture 112. The first aperture 104 defines a center, a first major axis, and a first minor axis, and is arranged to receive light from the output lens 68 via the first lens 108 and the reticle 96. The second aperture 112 defines a center, a second major axis, and a second minor axis, and is arranged to receive light from the first aperture 104 and project light via the second lens 116. The first major axis is larger than the second major axis, and the first minor axis is larger than the second minor axis.

A tool axis B is defined between the center of the first aperture 108 and the center of the second aperture 112. The tool axis B is arranged at an oblique tool angle C relative to the perpendicular optics axis A. In other words, the tool axis B is arranged at an oblique angle relative to the mating face 92 and/or the outlet 100. In the illustrated embodiment, the tool angle C is about thirty degrees (30°). The illustrated exit pupil locator tool 72 is arranged to interact with the helmet 46. In other embodiments, the tool angle C can be different depending on different lens prescriptions associated with different NED systems 20. For example, the optics are different in different helmets and the targeting feature 80 can be adapted to match the desired optics. In some embodiments, the relative sizes of the first and second major axis and first and second minor axis can be changed. In some embodiments, the tool angle C can be changed. In some embodiments, the first lens 108 and the second lens 116 can be changed or eliminated.

Figure 11:
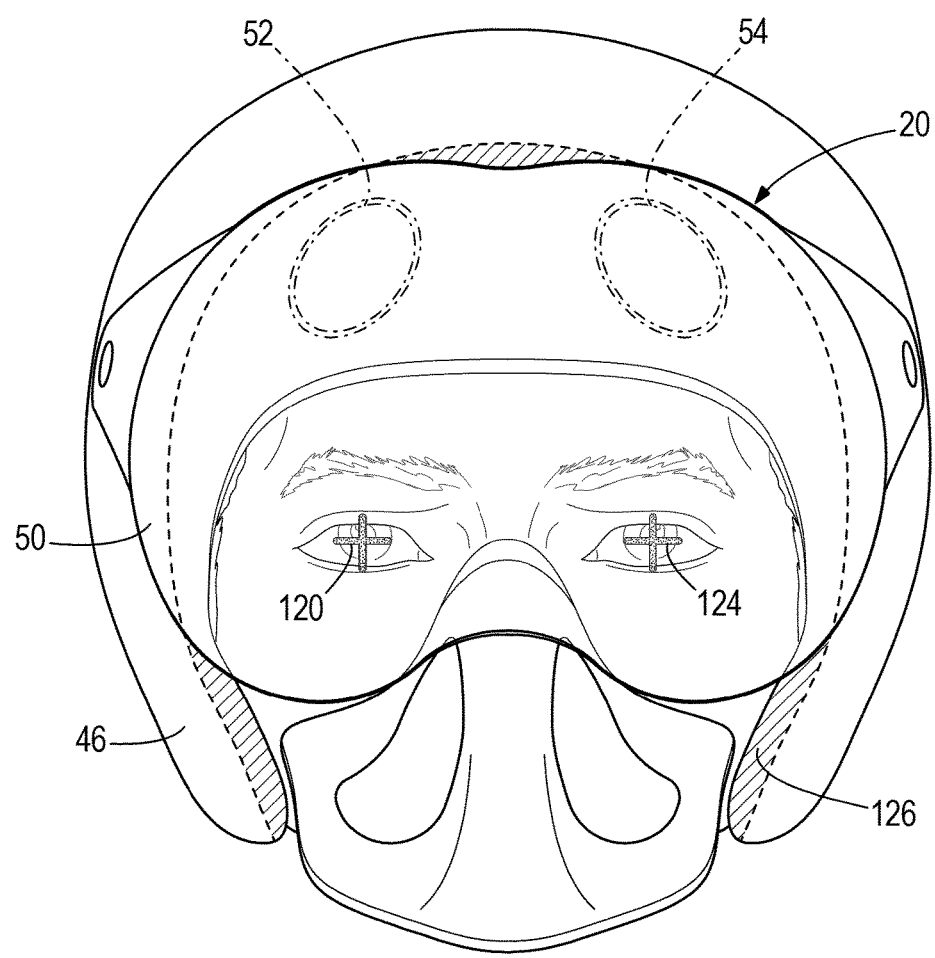
FIG. 11 is a front view of helmet of FIG. 1 including targeting images projected onto a user's eyes.

As shown in FIG. 11, when the exit pupil locator tool 72 is installed a first targeting image 120 is produced by the first optics component 52 and a second targeting image 124 is produced by the second optics component 54. The targeting images 120, 124 take on the shape defined by the reticle 96 and improve the fitters ability to center the exit pupils 56, 60 on the user's eyes. With the exit pupil locator tool 72 installed, consistent fitments can be achieved by fitters of varying skill and within a tolerance of about two millimeters (2 mm). In other embodiments, a tolerance of about four millimeters (4 mm) is achieved. In still other embodiments, a tolerance of about eight millimeters (8 mm) is achieved. A custom liner 126 can be adjusted or modified to adjust the location of the targeting images 120, 124 relative to the user's eyes. In some embodiments, material is either added to or removed from the custom liner during adjustment. In some embodiments, the custom liner includes a plurality of separate pads that work together as a padding system.

Figure 12:
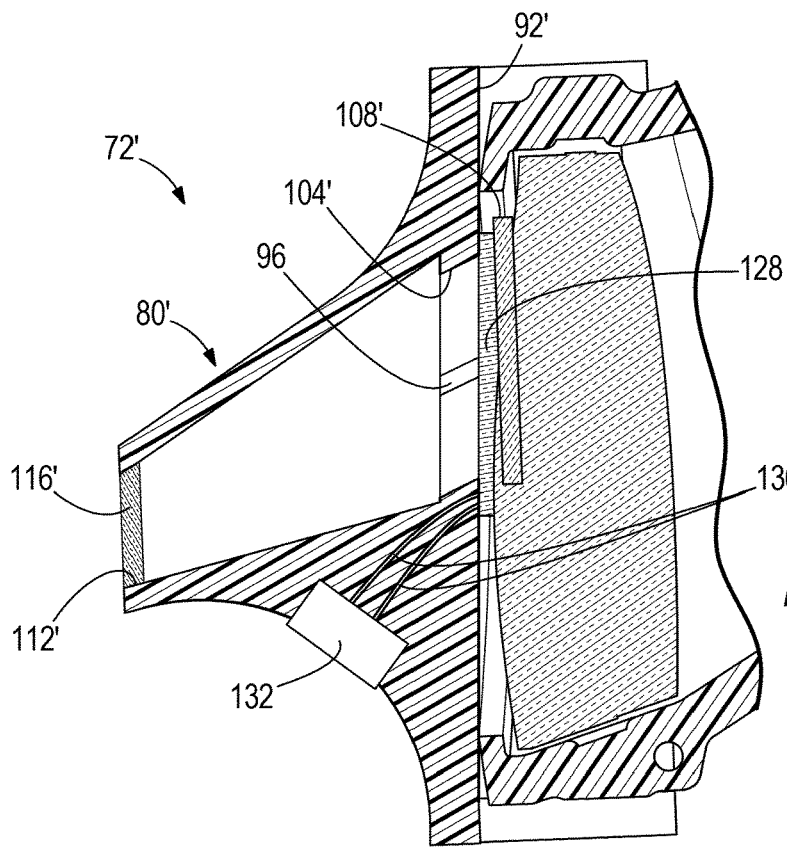
FIG. 12 is a cross sectional view of an exit pupil locator according to another embodiment.

As shown in FIG. 12, an exit pupil locator tool 72' is similar to the exit pupil locator tool 72 discussed above and like parts are labeled with like reference numbers in the prime series. The exit pupil locator tool 72' additionally includes a light source 128, that is connected to a battery 132, by leads 136. The exit pupil locator tool 72' can be used to fit the helmet 46 without operating the HMD system 20. During fitting the fitter, activates the light source 128, and light is projected through the targeting feature 80 and the targeting images 120, 124 are displayed on the user's eyes. In one embodiment, the light source 128 is a circular led array.

Figure 13:
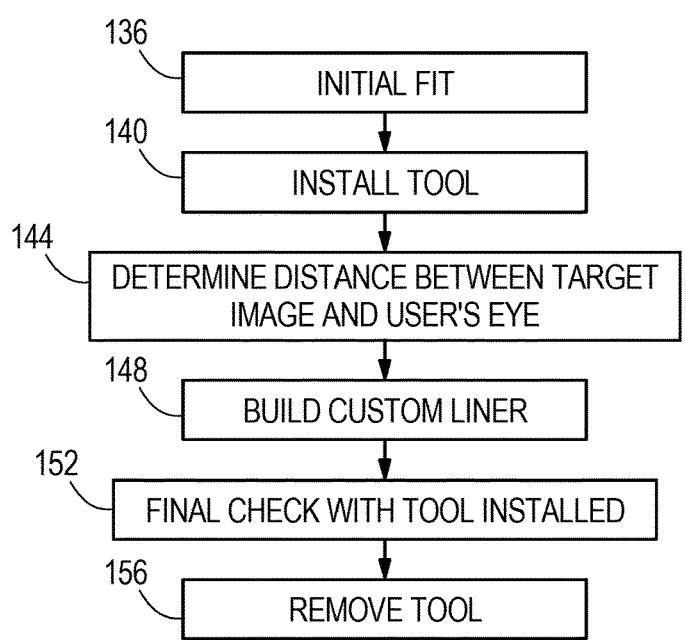
FIG. 13 is a flow diagram of a fitting operation for the HMD of FIG. 2 according to another embodiment.

As shown in FIG. 13, a method of fitting an HMD system 20 includes an initial fitting at step 136 wherein the helmet 46 is generally sized for the user's head. After the initial fitting, one exit pupil locator tool 72 is installed on each optics component 52, 54 at step 140. With the exit pupil locator tool 72 installed, the HMD system 20 is activated, or alternatively, the light source 128 is activated in the case of the exit pupil locator tool 72'. With the targeting images 120, 124 displayed on the user's eyes, a differential distance between the center of the targeting images 120, 124 and the user's eyes or pupils id determined at step 144.

With the differential distance determined, custom liners or pads can be produced and installed in the helmet 46 at step 148. With the custom liner installed, a final check is executed with the exit pupil locator tools 72 installed at step 152. If the differential distances between the targeting images 120, 124 and the user's eyes or pupils is within a predetermined tolerance (e.g., 2 mm, 4 mm, or 8 mm), then the exit pupil locator tools 72 are removed at step 156 and the fitting is complete. If more adjustment is necessary, the custom liner can be adjusted, and the final check redone at step 152 until the differential distance is found to be within the predetermined tolerance.

As discussed above, the exit pupil locator tool 72 and the exit pupil locator tool 72' may be used on monocular and binocular systems. Additionally, using the exit pupil locator tool 72 or the exit pupil locator tool 72' requires no modification of the HMD system 20. In one embodiment, the exit pupil locator tool 72, 72' is 3D printed from a plastic. In other embodiments, the exit pupil locator tool 72, 72' is injection molded or produced using another method.

While the detailed drawings, specific examples, detailed algorithms and particular configurations given describe preferred and exemplary embodiments, they serve the purpose of illustration only. The inventions disclosed are not limited to the specific forms and reticles shown. For example, the methods may be performed in any of a variety of sequence of steps. The hardware and optical configurations shown and described may differ depending on the chosen performance characteristics and physical characteristics of the weather radar and processing devices. For example, the type of system components and their interconnections may differ. The systems and methods depicted and described are not limited to the precise details and conditions disclosed. The flow charts show preferred exemplary operations only. The specific mechanical components and operations are shown in a non-limiting fashion. Furthermore, other substitutions, modifications, changes, and omissions may be made in the design, operating conditions, and arrangement of the exemplary embodiments without departing from the scope of the invention as expressed in the appended claims.

What is claimed is:

1. An exit pupil locator tool for a helmet comprising:
   wherein the helmet comprises a helmet mounted display having a computer, an image source, an optics component, and a combiner;
   wherein the tool comprises
   a connector configured to engage the optics component defining an optics axis of the helmet mounted display; and
   a target comprising a reticle, a first aperture, and a second aperture and defining a tool axis arranged at an oblique tool angle relative to the optics axis.

2. The exit pupil locator tool of claim 1, wherein the connector comprises a tab configured to engage the optics component with a press fit.

3. The exit pupil locator tool of claim 1, wherein the connector comprises a recess sized to receive a projection formed on the optics component.

4. The exit pupil locator tool of claim 1, wherein the reticle defines an X shape.

5. The exit pupil locator tool of claim 1, wherein the first aperture and the second aperture are generally oval shaped.

6. The exit pupil locator tool of claim 1, wherein the first aperture is larger than the second aperture.

7. The exit pupil locator tool of claim 6, wherein the tool angle is about thirty degrees.

8. The exit pupil locator tool of claim 1, further comprising a first lens positioned adjacent the first aperture and a second lens positioned adjacent the second aperture.

9. The exit pupil locator tool of claim 1, further comprising a first lens associated with the first aperture and positioned upstream of the reticle.

10. The exit pupil locator tool of claim 1, further comprising a light source arranged upstream of the reticle.

11. The exit pupil locator tool of claim 10, further comprising a battery providing power to the light source.

12. The exit pupil locator tool of claim 10, wherein the exit pupil locator tool is three dimensionally printed from a plastic.

13. A fitting system for a helmet comprising a helmet mounted display having a computer, an image source, an optical component, and a combiner, the fitting system comprising:
    an exit pupil locator tool comprising:
    a connecting feature configured to engage the optical component; and
    a reticle configured to receive light from the optical component;
    and wherein the exit pupil locator tool has:
    a first aperture positioned adjacent to the reticle to receive light from the reticle; and
    a second aperture positioned downstream of the first aperture and configured to project a targeting image onto the combiner.

14. The fitting system of claim 13, wherein the reticle is substantially X shaped.

15. The fitting system of claim 13, wherein the first aperture is larger than the second aperture.

16. The fitting system of claim 13, wherein the optical component defines an optics axis, and wherein the exit pupil locator tool defines a tool axis arranged at an oblique tool angle relative to the optics axis.

17. The fitting system of claim 13, further comprising a light source separate from the optics component and arranged to provide light to the reticle.

18. A method of fitting a helmet comprising a helmet mounted display, the method comprising:
    installing an exit pupil locator tool onto an optics component of the helmet mounted display, where the exit pupil locator tool comprises a connector configured to engage the optics component of the helmet mounted display, and a target comprising a reticle, the exit pupil locator tool having a first aperture and a second aperture;
    projecting light into the exit pupil locator tool;
    projecting a reticle shaped targeting image onto a combiner of the helmet mounted display with the exit pupil locator tool;
    observing a reflection of the targeting image on a user's eye; and
    determining a differential distance between a center of the targeting image and the user's eye.

19. The method of claim 18, further comprising:
    constructing a custom liner for the helmet based at least in part of the determined differential distance.

20. The method of claim 18, further comprising:
    using the exit pupil locator tool to confirm alignment of the targeting image and the user's eye; and
    removing the exit pupil locator tool from the optics component.

* * * * *